(12) United States Patent
Fujiwara et al.

(10) Patent No.: US 11,534,119 B2
(45) Date of Patent: Dec. 27, 2022

(54) ANALYSIS APPARATUS AND ANALYSIS PROGRAM (71) Applicants: CANON MEDICAL SYSTEMS CORPORATION, Otawara (JP); National Institutes for Quantum Science and Technology, Chiba (JP); General Incorporated Association The Japan-Multinational Trial Organization, Nagoya (JP)

(72) Inventors: Shunsuke Fujiwara, Utsunomiya (JP); Yasuo Sakurai, Nasushiobara (JP); Ming-Rong Zhang, Chiba (JP); Lin Xie, Chiba (JP); Masayuki Fujinaga, Chiba (JP); Masayuki Hanyu, Chiba (JP); Cheng-Long Huang, Nagoya (JP); Masakazu Fukushima, Nagoya (JP); Hiromi Wada, Nagoya (JP)

(73) Assignees: CANON MEDICAL SYSTEMS CORPORATION, Otawara (JP); National Institutes for Quantum Science and Technology, Chiba (JP); General Incorporated Association The Japan-Multinational Trial Organization, Nagoya (JP)

( * ) Notice: Subject to any disclaimer, the term of this patent is extended or adjusted under 35 U.S.C. 154(b) by 0 days.

(21) Appl. No.: 17/081,564

(22) Filed: Oct. 27, 2020

(65) Prior Publication Data
US 2021/0128089 A1 May 6, 2021

(30) Foreign Application Priority Data
Oct. 31, 2019 (JP) .............. JP2019-198958
Oct. 23, 2020 (JP) .............. JP2020-178434

(51) Int. Cl.
A61B 6/00 (2006.01)
A61B 6/03 (2006.01)

(52) U.S. Cl.
CPC ............ A61B 6/4057 (2013.01); A61B 6/508 (2013.01); A61B 6/037 (2013.01)

(58) Field of Classification Search
None
See application file for complete search history.

(56) References Cited

U.S. PATENT DOCUMENTS

2016/0263258 A1* 9/2016 Lee ................... A61K 51/0455
2017/0100493 A1* 4/2017 Sander .............. A61K 31/4745
2021/0049793 A1* 2/2021 Zhu ....................... G06T 7/0016

FOREIGN PATENT DOCUMENTS

JP 2015-044803 A 3/2015

OTHER PUBLICATIONS

Sugae et al., "Fluorine-18-labeled 5-fluorouracil is a useful radiotracer for differentiation of malignant tumors from inflammatory lesions" Annals of Nuclear Medicine (2008), 22(1):65-72 (Year: 2008).*

(Continued)

Primary Examiner — Colin T. Sakamoto
(74) Attorney, Agent, or Firm — Oblon, McClelland, Maier & Neustadt, L.L.P.

(57) ABSTRACT

An analysis apparatus according to an embodiment includes an extraction unit, a calculation unit, and an evaluation unit. The extraction unit extracts a detection value in a tumor region, a blood region, and a muscle region from a nuclear medicine image of a subject administered with a drug containing a radiolabeled anticancer drug that works by accumulating in a tumor. The calculation unit calculates a first comparison value that is a comparison result between the detection value in the blood region and the detection value in the tumor region, and a second comparison value that is a comparison result between the detection value in the (Continued)

muscle region and the detection value in the tumor region. The evaluation unit evaluates an accumulation of the drug in the tumor, based on the first comparison value and the second comparison value calculated by the calculation unit.

16 Claims, 5 Drawing Sheets

(56) References Cited

OTHER PUBLICATIONS

Johnston et al., "Thymidylate Synthase Gene and Protein Expression Correlate and Are Associated with Response to 5-Fluorouracil in Human Colorectal and Gastric Tumors", Cancer Research 55, Apr. 1, 1995, pp. 1407-1412.

Tsutani et al., "Decreased orotate phosphoribosyltransferase activity produces 5-fluorouracil resistance in a human gastric cancer cell line", Oncology Reports 20, 2008, pp. 1545-1551.

* cited by examiner

ANALYSIS APPARATUS AND ANALYSIS PROGRAM

CROSS-REFERENCE TO RELATED APPLICATIONS

This application is based upon and claims the benefit of priority from Japanese Patent Application No. 2019-198958, filed on Oct. 31, 2019 and Japanese Patent Application No. 2020-178434, filed on Oct. 23, 2020; the entire contents of which are incorporated herein by reference.

FIELD

Embodiments described herein relate generally to an analysis apparatus and an analysis program.

BACKGROUND

Conventionally, to select a suitable anticancer drug for the patient, a test is performed to detect a specific biological substance such as a gene and protein. In particular, to predict the pharmacological efficacy of 5-fluorouracil (FU), which is an antimetabolite, a relation between the expression level of thymidylate synthase (TS), which is an inhibitory target of 5-FU, and the sensitivity of 5-FU has been reported. Thus, it is assumed that the pharmacological efficacy of 5-FU can be predicted to some degree, by evaluating the expression level of TS in pathological tissues of patients.

However, to evaluate the expression level of TS, pathological tissues of patients are generally obtained by tissue biopsy, and the obtained pathological tissues are stained by a certain staining method. Thus, the evaluation of the expression level of TS is highly invasive, and a large load is placed on the patient. Moreover, in the tissue biopsy, only a part of tumor is removed. Thus, with the evaluation of the expression level of TS, it is difficult to evaluate the comprehensive kinetics of 5-FU in vivo and the pharmacological efficacy of 5-FU in heterogeneous tumors.

DETAILED DESCRIPTION

Hereinafter, an embodiment of an analysis apparatus and an analysis program will be described in detail with reference to the accompanying drawings. However, the embodiment is not limited to the following embodiment.

Embodiment

An analysis apparatus according to an embodiment includes an extraction unit, a calculation unit, and an evaluation unit. The extraction unit extracts a detection value in a tumor region, a blood region, and a muscle region from a nuclear medicine image of a subject administered with a drug containing a radiolabeled anticancer drug that works by accumulating in a tumor. The calculation unit calculates a first comparison value that is a comparison result between the detection value in the blood region and the detection value in the tumor region, and a second comparison value that is a comparison result between the detection value in the muscle region and the detection value in the tumor region. The evaluation unit evaluates an accumulation of the drug in the tumor, based on the first comparison value and the second comparison value calculated by the calculation unit. The first comparison value may also be a ratio between the detection value in the blood region and the detection value in the tumor region. The second comparison value may also be a ratio between the detection value in the muscle region and the detection value in the tumor region.

Figure 1:
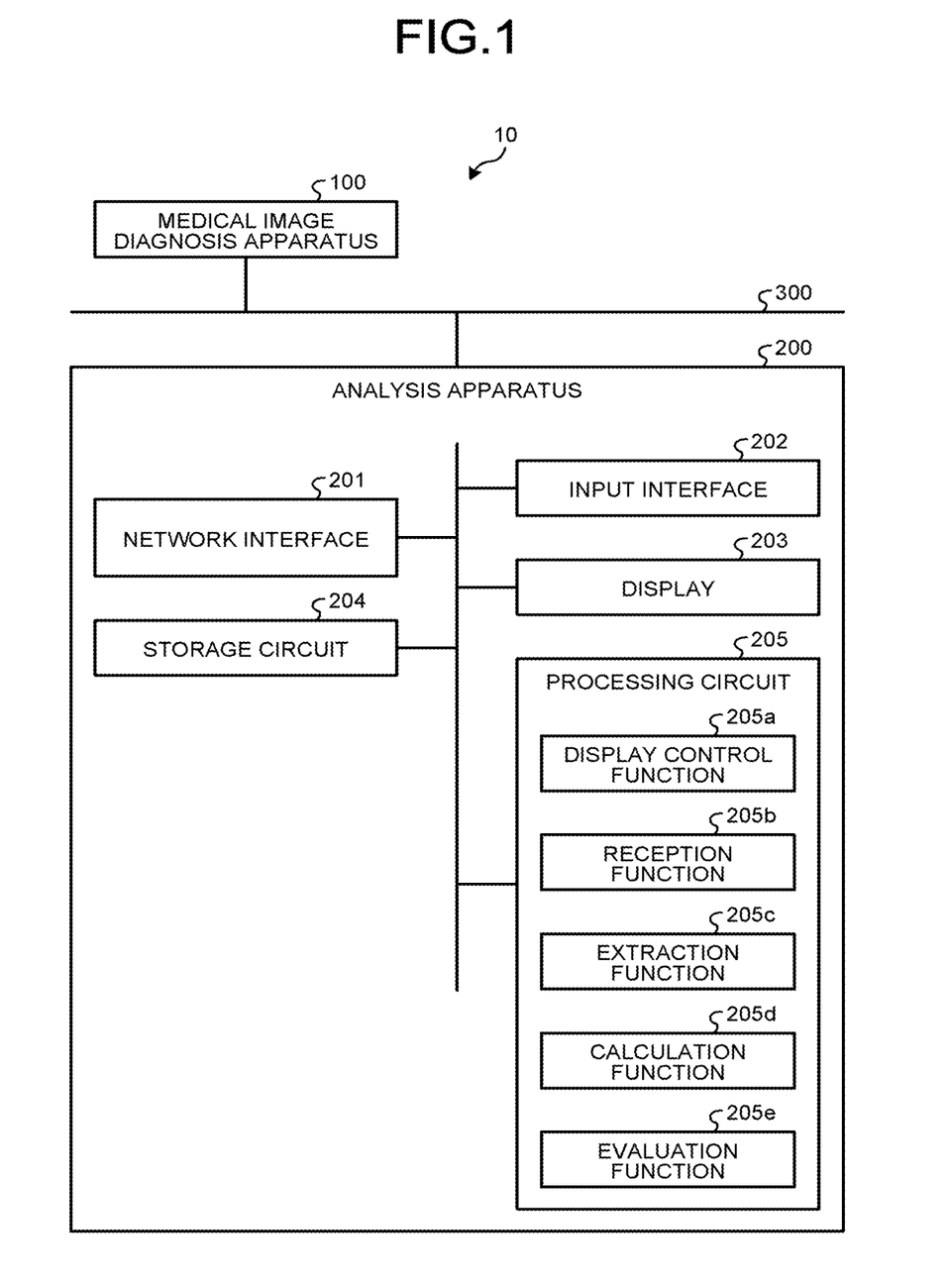
FIG. 1 is a block diagram illustrating a configuration example of a medical image diagnosis system according to an embodiment.

FIG. 1 is a block diagram illustrating a configuration example of a medical image diagnosis system according to an embodiment. As illustrated in FIG. 1, a medical image diagnosis system 10 according to the embodiment includes a medical image diagnosis apparatus 100 and an analysis apparatus 200. For example, the medical image diagnosis apparatus 100 and the analysis apparatus 200 are communicably connected via a network 300 such as an in-hospital local area network (LAN).

In the following embodiment, the medical image diagnosis apparatus 100 is a PET-CT apparatus in which a positron emission computed tomography (PET) apparatus and an X-ray computed tomography (CT) apparatus are integrally formed. However, the embodiment is not limited thereto, and for example, the medical image diagnosis apparatus 100 may also be the PET apparatus. Moreover, when the PET apparatus is used as the medical image diagnosis apparatus 100, the medical image diagnosis system 10 may also include the X-ray CT apparatus serving as a medical image diagnosis apparatus different from the medical image diagnosis apparatus 100.

The medical image diagnosis apparatus 100 is an apparatus for capturing medical images. The medical image diagnosis apparatus 100 captures a medical image depicting the inside of a subject, and transmits the captured medical image to the analysis apparatus 200. For example, the medical image diagnosis apparatus 100 captures a PET image depicting the inside of a subject with a tumor to which the anticancer drug 5-FU labelled with the positron-emitting radionuclide 18F ([18F]5-FU) is administered. The medical image diagnosis apparatus 100 also transmits the captured PET image to the analysis apparatus 200. More specifically, the medical image diagnosis apparatus 100 captures a PET image of a subject with a tumor to which [18F]5-FU is administered and after a predetermined time has elapsed from the administration, and transmits the captured PET image to the analysis apparatus 200. Moreover, the medical image diagnosis apparatus 100 captures a CT image depicting the inside of a subject with a tumor, and transmits the captured CT image to the analysis apparatus 200. A 5-FU degrading enzyme inhibitor may also be administered to the subject with [18F]5-FU. [18F]5-FU is an example of a drug containing radiolabeled 5-FU that is an anticancer drug that works by accumulating in a tumor. Whether the subject have a tumor may be unknown. The PET image is an example of a nuclear medicine image.

The analysis apparatus 200 acquires medical images via the network 300, and executes various processes using the acquired medical images. For example, the analysis apparatus 200 acquires a PET image and a CT image of a subject with a tumor to which [18F]5-FU is administered, via the network 300. The analysis apparatus 200 then executes various processes using the acquired PET image and CT image. The analysis apparatus 200 executes processing functions to evaluate the comprehensive kinetics of 5-FU in vivo and the pharmacological efficacy of 5-FU, without placing a burden on a patient. For example, the analysis apparatus 200 is implemented by a computer apparatus such as a workstation.

As illustrated in FIG. 1, the analysis apparatus 200 includes a network interface 201, an input interface 202, a display 203, a storage circuit 204, and a processing circuit 205. The network interface 201, the input interface 202, the display 203, the storage circuit 204, and the processing circuit 205 are connected with each other.

The network interface 201 receives medical images. The medical images received by the network interface 201 will be stored in the storage circuit 204.

The input interface 202 receives various input operations from an operator, coverts the received input operations to electric signals, and outputs the converted signals to the processing circuit 205. For example, the input interface 202 is implemented by a mouse, a keyboard, a trackball, a switch, a button, a joystick, a touch pad on which an input operation can be performed by touching the operation surface, a touch screen in which a display screen and the touch pad are integrally formed, a non-contact input circuit using an optical sensor, a voice input circuit, and the like. The input interface 202 is not limited to that including a physical operation component such as a mouse and a keyboard. For example, the input interface 202 also includes an electric signal processing circuit that receives an electric signal corresponding to an input operation from an external input apparatus provided separately from the analysis apparatus 200, and that outputs electric signals to the processing circuit 205.

The display 203 displays various types of information. For example, under the control of the processing circuit 205, the display 203 displays a medical image and the like. The display 203 displays a graphical user interface (GUI) for receiving various instructions, various settings, and the like from an operator via the input interface 202. For example, the display 203 is a liquid crystal display and a cathode ray tube (CRT) display. The display 203 may be a desktop type, or may be configured by a tablet terminal and the like wirelessly communicable with the analysis apparatus 200 main body. The display 203 is an example of a display unit.

For example, the storage circuit 204 is implemented by a semiconductor memory element such as a random access memory (RAM) and a flash memory, or a hard disk, an optical disc, and the like. The storage circuit 204 may also be used as a non-transitory storage medium by hardware. The storage circuit 204 stores therein acquired medical image data. Moreover, for example, the storage circuit 204 stores therein a computer program enabling the circuit in the analysis apparatus 200 to execute the function. The storage circuit 204 is an example of a storage unit.

The processing circuit 205 controls the entire process of the analysis apparatus 200. More specifically, the processing circuit 205 includes a display control function 205a, a reception function 205b, an extraction function 205c, a calculation function 205d, and an evaluation function 205e. The display control function 205a is an example of a display control unit. The reception function 205b is an example of a reception unit. The extraction function 205c is an example of an extraction unit. The calculation function 205d is an example of a calculation unit. The evaluation function 205e is an example of an evaluation unit.

In this example, for example, the processing functions of the display control function 205a, the reception function 205b, the extraction function 205c, the calculation function 205d, and the evaluation function 205e that are components of the processing circuit 205 are stored in the storage circuit 204 in the form of computer programs that can be executed by a computer. The processing circuit 205 executes the function corresponding to each of the computer programs, by reading out each computer program from the storage circuit 204, and executing the read computer program. In other words, the processing circuit 205 that has read out the computer programs has the functions indicated in the processing circuit 205 in FIG. 1. In FIG. 1, each processing function of the display control function 205a, the reception function 205b, the extraction function 205c, the calculation function 205d, and the evaluation function 205e is implemented by a single processing circuit 205. However, it is not limited thereto, and the processing circuit 205 may be configured by combining a plurality of individual processors, and each processing function may be implemented by each processor executing each computer program.

For example, the term "processor" used in the above description indicates a circuit such as a central processing unit (CPU), a graphics processing unit (GPU), an application specific integrated circuit (ASIC), a programmable logic device (for example, a simple programmable logic device (SPLD), a complex programmable logic device (CPLD), and a field programmable gate array (FPGA)), or the like. Instead of storing a computer program in the storage circuit 204, a computer program may also be directly incorporated in the circuit of the processor. In this case, the function is implemented when the processor reads out and executes the computer program incorporated in the circuit.

The display control function 205a causes the display 203 to display various GUIs, medical images, or the like. For example, the display control function 205a causes the display 203 to display various GUIs, PET images, CT images, superimposed images of a PET image and a CT image, and the like.

The reception function 205b receives various operations by an operator via the input interface 202. For example, the reception function 205b receives an operation of setting a region of interest in a tissue region performed by an operator, via the input interface 202. More specifically, the reception function 205b receives an operation of setting a region of interest in a tumor region, a cardiac region, and a muscle region performed by an operator, via the input interface 202. The reception function 205b sends the received region of interest to the extraction function 205c. The cardiac region is an example of a blood region.

The extraction function 205c extracts the radioactivity level in the region of interest set in the tissue region, from the PET image of a subject with a tumor to which [18F]5-FU is administered. For example, the extraction function 205c extracts the radioactivity level (for example, average radioactivity level) in a region of interest set in the tumor region (tumor interest region), a region of interest set in the cardiac region (cardiac interest region), and a region of interest set in the muscle region (muscle interest region) from the PET image of a subject with a tumor to which [18F]5-FU is administered. The radioactivity level is an example of a detection value.

The calculation function 205d calculates a first ratio that is a ratio of the radioactivity level in the tumor interest region to the radioactivity level in the cardiac interest region and a second ratio that is a ratio of the radioactivity level in the tumor interest region to the radioactivity level in the muscle interest region from the radioactivity level in each of the tumor interest region, the cardiac interest region, and the muscle interest region, extracted by the extraction function 205c. The first ratio is an example of a ratio between the detection value in the blood region and the detection value in the tumor region. The second ratio is an example of a ratio between the detection value in the muscle region and the detection value in the tumor region.

The evaluation function 205e evaluates the specificity of accumulation of [18F]5-FU in the tumor, by using the first ratio and the second ratio calculated by the calculation function 205d. For example, the evaluation function 205e evaluates whether [18F]5-FU is easily accumulated in the tumor, by comparing the first ratio and the second ratio that are calculated by the calculation function 205d, with a predetermined threshold (for example, 1 and the like). For example, the threshold may also be set on the basis of the first ratio and the second ratio obtained from a certain number of patients. To evaluate the specificity from the first ratio and the second ratio is an example of evaluating the accumulation of a drug in the tumor, based on a ratio between the detection value in the blood region and the detection value in the tumor region, and a ratio between the detection value in the muscle region and the detection value in the tumor region.

Figure 2:
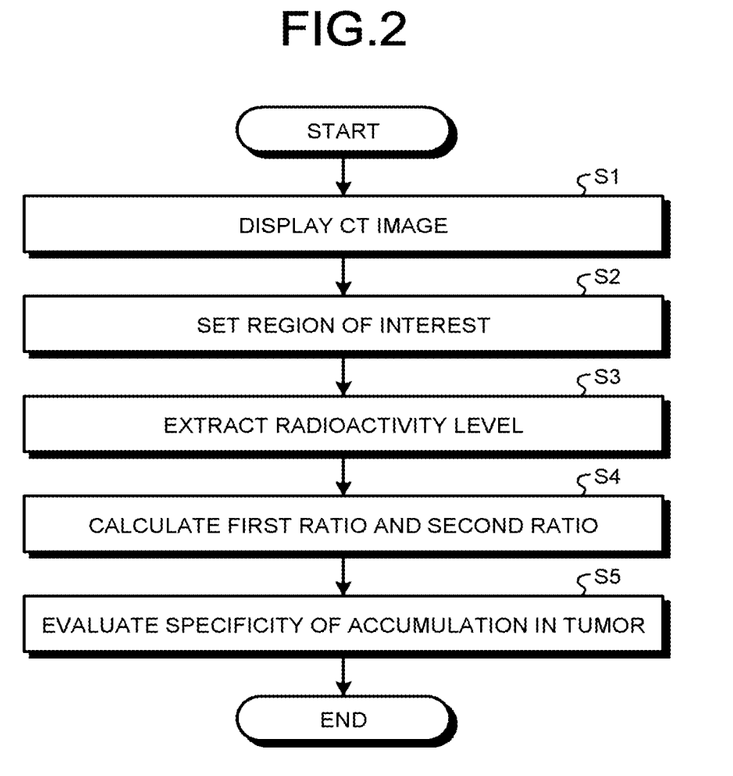
FIG. 2 is a flowchart illustrating an example of a processing flow executed by an analysis apparatus according to the embodiment.

Next, an example of a processing flow executed by the analysis apparatus 200 according to the embodiment will be described. FIG. 2 is a flowchart illustrating an example of a processing flow executed by the analysis apparatus 200 according to the embodiment. In this example, it is assumed that a PET image and a CT image of a subject with a tumor to which [18F]5-FU is administered and after a predetermined time has elapsed from the administration are captured by the medical image diagnosis apparatus 100, and are stored in the storage circuit 204 in advance.

First, the display control function 205a causes the display 203 to display a CT image stored in the storage circuit 204 (S1). The display control function 205a may also cause the display 203 to display a superimposed image of a PET image and a CT image.

The operator identifies the positions of the tumor, the heart as a blood pool, and the muscle of the subject, in the CT image displayed on the display 203. The operator then performs an operation of setting a region of interest in the tumor region, cardiac region and muscle region in the image, via the input interface 202. When a superimposed image is displayed on the display 203, the operator identifies the positions of the tumor, the heart as a blood pool, and the muscle of the subject, in the superimposed image, and performs an operation of setting a region of interest in the tumor region, cardiac region, and muscle region in the image.

Next, the reception function 205b receives the setting of the region of interest in the tumor region, cardiac region, and muscle region performed by the operator, and sends the setting of the received regions of interest (tumor interest region, cardiac interest region, and muscle interest region) to the extraction function 205c (S2).

In this example, the region of interest is set manually. However, it is not limited thereto, and the region of interest may also be set automatically. For example, the region of interest may be set in an image, by extracting the contour of a structure in an image by a known segmentation process, and on the basis of the position and shape of the extracted contour.

Next, the extraction function 205c extracts the average radioactivity level in the set tumor interest region, cardiac interest region, and muscle interest region, from the PET image (S3).

Next, the calculation function 205d calculates a first ratio that is a ratio of the average radioactivity level in the tumor interest region to the average radioactivity level in the cardiac interest region and a second ratio that is a ratio of the average radioactivity level in the tumor interest region to the average radioactivity level in the muscle interest region from the average radioactivity level in each of the extracted tumor interest region, cardiac interest region, and muscle interest region (S4).

Next, when the calculated first ratio and second ratio are both greater than a predetermined threshold, the evaluation function 205e evaluates that [18F]5-FU is easily accumulated in the tumor, and when at least one of the calculated first ratio and second ratio is smaller than a predetermined threshold, the evaluation function 205e evaluates that [18F]5-FU does not easily accumulate in the tumor (S5). Alternatively, when one of the first ratio and the second ratio is smaller than a predetermined threshold, the evaluation function 205e may evaluate that [18F]5-FU is moderately accumulated in the tumor, and when both of the first ratio and the second ratio are smaller than a predetermined threshold, the evaluation function 205e may evaluate that [18F]5-FU does not easily accumulate in the tumor.

With reference to the evaluation results obtained by the analysis apparatus 200, doctors can determine whether to apply a treatment with 5-FU to a subject to be evaluated, or whether to apply a treatment other than the treatment with 5-FU to the subject to be evaluated.

In this manner, in the embodiment, the specificity of accumulation of [18F]5-FU in the tumor is evaluated, by calculating the first ratio that is a ratio of the radioactivity level in the tumor region to the radioactivity level in the cardiac region and the second ratio that is a ratio of the radioactivity level in the tumor region to the radioactivity level in the muscle region from the radioactivity level in each of the tumor region, cardiac region, and muscle region, extracted from the PET image of a subject with a tumor to which [18F]5-FU is administered; and by using the calculated first ratio and second ratio. Consequently, with the embodiment, it is possible to evaluate the comprehensive kinetics of 5-FU in vivo and the pharmacological efficacy of 5-FU, without placing a burden on the patient.

More specifically, with the embodiment, it is possible to evaluate the accumulated state of 5-FU in the tumor, without placing a burden on the patient. Moreover, with the embodiment, it is possible to prevent 5-FU from being administered to a patient who cannot expect therapeutic effects from 5-FU. In addition, it is possible to prevent side effects. Moreover, with the embodiment, it is possible to easily evaluate a change in the kinetics of 5-FU in vivo caused by the acquisition of resistance against 5-FU due to the continuous administration of 5-FU. Furthermore, with the present embodiment, it is possible to prevent the progression of cancer caused by the continuous administration of 5-FU to a patient who cannot expect therapeutic effects from 5-FU. Still furthermore, with the embodiment, it is possible to help doctors to determine and switch to a suitable anticancer drug.

The embodiment of the present invention has been described. However, the embodiment is merely an example, and is not intended to limit the scope of the invention. The embodiment may be implemented in various other forms, and various omissions, replacements, and changes may be made without departing from the scope of the invention. The embodiment and the modifications are included in the scope and gist of the invention, and are included in the invention described in the claims and the equivalents thereof.

Example 1. Visualization of Kinetics of 5-FU in Vivo Using [18F]5-FU

Visualization of kinetics of 5-FU in vivo using [18F]5-FU was attempted, by performing an experiment with the following procedures 11 to 15, on DLD-1 mice (N=8) and DLD-1/5-FU mice (N=8).

In this example, the DLD-1 mice are cancer-bearing mice with a tumor (average tumor volume 107 $mm^3$) derived from a colon cancer cell line DLD-1. The DLD-1/5-FU mice are cancer-bearing mice with a tumor derived from a colon cancer cell line DLD-1/5-FU (average tumor volume 86 $mm^3$). DLD-1/5-FU is established by culturing DLD-1 in a culture medium added with 5-FU. The sensitivity of DLD-1 and DLD-1/5-FU to 5-FU is different. DLD-1 is sensitive to 5-FU, and DLD-1/5-FU is resistant to 5-FU.

Figure 3:
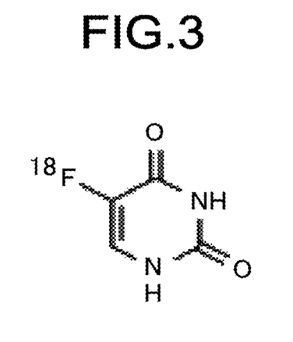
FIG. 3 is a diagram illustrating a structural formula of [18F]5-FU.

Procedure 11. Administer 18 MBq of [18F]5-FU (see FIG. 3) per mouse and 10 mg/kg of gimeracil (5-FU degrading enzyme inhibitor) per mouse by injection into the tail vein of the mice at the same time. The dosage of 18 MBq of [18F]5-FU corresponds to the dosage of 1.5 pg/kg of 5-FU.

Procedure 12. At the point about 45 minutes after administration, anesthetize the mice, and fix each of the mice to an image capturing table.

Procedure 13. At 50 minutes after administration, capture an image of the mouse by static scanning for 10 minutes, using a PET apparatus (manufactured by Canon Medical Systems Corporation).

Procedure 14. After capturing an image of the mouse by the PET apparatus, move the image capturing table on which the mouse is fixed to an X-ray CT apparatus (manufactured by Canon Medical Systems Corporation), and capture an image of the mouse by the X-ray CT apparatus.

Procedure 15. Perform PET imaging using a viewer (software) for medical image analysis. The viewer is implemented in a computer connected with the PET apparatus and the X-ray CT apparatus, and can set a region of interest and extract the average radioactivity level (% ID/g and standardized uptake value (SUV)) in the region of interest. More specifically, perform PET imaging on a predetermined operation screen that is displayed on the display of the computer, and that is provided by the viewer; by inputting the body weight of the mouse, the dosage of [18F]5-FU, the dosage time, and the image capturing start time, and by setting the contrast of the image in the range of 0.5 to 2.0% ID/g wt.

Figure 4A:
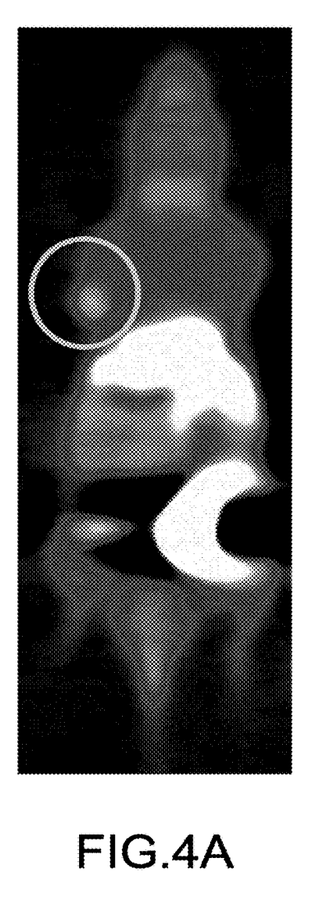
FIG. 4A is a diagram illustrating an example of a PET image of a DLD-1 mouse to which [18F]5-FU is administered.
Figure 4B:
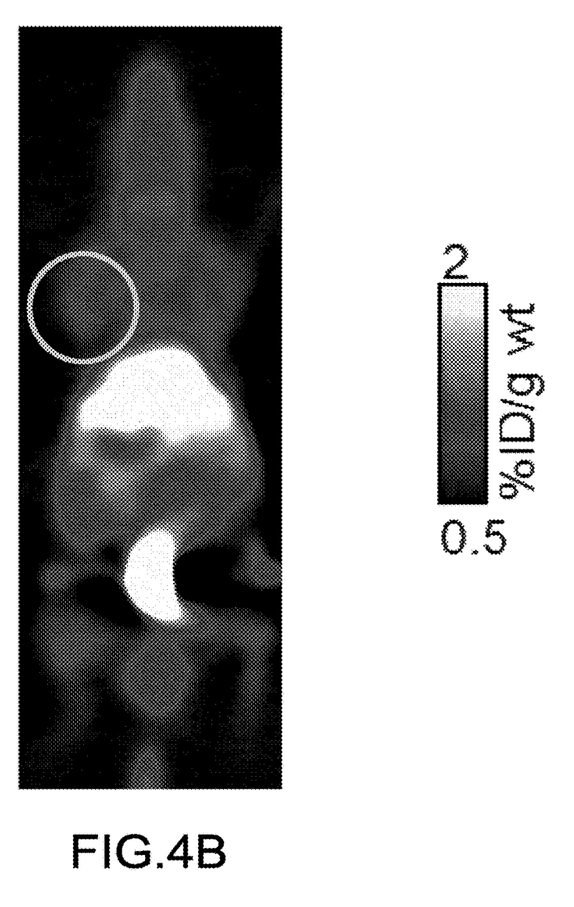
FIG. 4B is a diagram illustrating an example of a PET image of a DLD-1/5-FU mouse to which [18F]5-FU is administered.

FIG. 4A and FIG. 4B are examples of PET images obtained by the experiment. The image illustrated in FIG. 4A is a PET image of a DLD-1 mouse. The image illustrated in FIG. 4B is a PET image of a DLD-1/5-FU mouse. In each diagram, the circled region corresponds to a tumor region. From the PET images, it was possible to visualize a clear difference in the accumulation amount of [18F] in the tumor derived from DLD-1 and in the tumor derived from DLD-1/5-FU.

Example 2. Evaluating Specificity of Accumulation of [18F]5-FU in Tumor

In Example 1, from the PET images, the accumulation of [18F] was only identified in the tumor derived from DLD-1.

However, the retention amount of [18F] throughout the body of mice may differ between individuals. For example, in an individual with a high accumulation of [18F] throughout the body, the entire PET image may be highlighted. Thus, it is sometimes difficult to determine the specific accumulation of [18F] in the tumor from the PET image. Alternatively, in an individual with a low accumulation of [18F] throughout the body, it is not possible to determine whether the PET image is not highlighted because [18F] is actually not accumulated in the tumor, or because the absolute accumulation of [18F] is small.

Thus, it is considered necessary to quantify the radioactivity in the tumor site from the PET image, and compare the quantified radioactivity of individuals.

However, the retention amount of radioactivity throughout the body differs depending on the individuals. Thus, it is not appropriate to only compare the radioactivity accumulation in the tumors between individuals.

Thus, in Example 2, on the basis of the radioactivity in the heart as a blood pool and in the muscle, the specificity of accumulation of [18F] in the tumor was relatively evaluated, by calculating the ratio of radioactivity in the tumor to the radioactivity in the heart (hereinafter, referred to as a "tumor-to-blood ratio"), and the ratio of radioactivity in the tumor to the radioactivity in the muscle (hereinafter, referred to as a "tumor-to-muscle ratio"), and by comparing the calculated tumor-to-blood ratio and tumor-to-muscle ratio between individuals.

The tumor-to-blood ratio and the tumor-to-muscle ratio of the mice used in Example 1 were calculated through the following procedures 21 to 24. From the calculated tumor-to-blood ratio and the tumor-to-muscle ratio of the mice, the average value of the tumor-to-blood ratio and the average value of the tumor-to-muscle ratio of the DLD-1 mice, and the average value of the tumor-to-blood ratio and the average value of the tumor-to-muscle ratio of the DLD-1/5-FU mice were calculated.

Procedure 21. By using the viewer, generate a superimposed image of a PET image and a CT image of a mouse.

Figure 5:
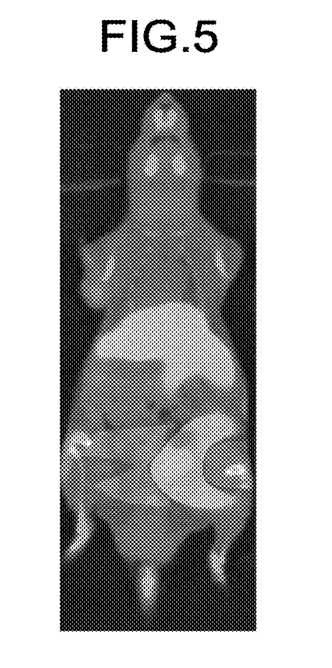
FIG. 5 is a diagram illustrating an example of a superimposed image of a CT image and a PET image.

Procedure 22. While observing the superimposed image (see FIG. 5), determine the regions of the tumor, heart, and muscle.

Procedure 23. On a predetermined operation screen provided by the viewer, set a region of interest in each of the determined regions, and by using the viewer, extract the average radioactivity level in each of the regions of interest.

Procedure 24. From the average radioactivity level in the extracted regions of interest, calculate the tumor-to-blood ratio and the tumor-to-muscle ratio.

From the calculated average value of the tumor-to-blood ratio and the average value of the tumor-to-muscle ratio of the DLD-1 mice and the DLD-1/5-FU mice, the specificity of accumulation of [18F] in the tumor was evaluated. In the DLD-1/5-FU mice, the average value of the tumor-to-blood ratio was 1.07, but in the DLD-1 mice, the value was significantly high at 1.99 (p<0.01). In the DLD-1/5-FU mice, the average value of the tumor-to-muscle ratio was 1.08, but in the DLD-1 mice, the value was significantly high at 2.14 (p<0.01). In other words, in the DLD-1 mice, the average value of the tumor-to-blood ratio was about 1.86 times higher and the average value of the tumor-to-muscle ratio was about 1.98 times higher than those of the DLD-1/5-FU mice. Both values were significantly high.

Moreover, to verify the validity of the comparison results of the tumor-to-blood ratio and the tumor-to-muscle ratio obtained from the PET image, comparisons were made on the radioactivity levels in the tumors obtained from the dissected tissues, the tumor-to-blood ratios, and the tumor-to-muscle ratios. More specifically, at each time point of 10 minutes after administration, 30 minutes after administration, 60 minutes after administration, and 240 minutes administration, four DLD-1 mice and four DLD-1/5-FU mice were prepared, and an experiment with the following procedures 31 to 34 was performed on the mice. Thus, quantitative comparisons were made on the radioactivity levels in the tumors of the DLD-1 mice and DLD-1/5-FU mice, and were also made on the tumor-to-blood ratios and the tumor-to-muscle ratios of the DLD-1 mice and DLD-1/5-FU mice. In the example, to obtain the tumor-to-blood ratio from the dissected tissues, the radioactivity in the actual blood sample was used as a reference, instead of using the radioactivity in the heart. Thus, the tumor-to-blood ratio obtained from the dissected tissues is a ratio of radioactivity in the tumor to the radioactivity in the blood.

Procedure 31. Administer 1.8 MBq of [18F]5-FU per mouse, and 10 mg/kg of gimeracil per mouse by injection into the tail vein of the mice at the same time.

Procedure 32. After reaching the time point, promptly dissect the mice, and analyze the radioactivity distribution in tissues (tumor, blood, muscle, lung, bone, and the like). More specifically, promptly perform the work of dissecting the mice, separating the tissues from the mice, and measuring the weight of the separated tissues and the radioactivity levels in the separated tissues.

Procedure 33. Calculate the radioactivity level per unit weight of each tissue, from the measured weight of the tissues and the radioactivity levels in the tissues.

Procedure 34. Calculate the tumor-to-blood ratio and the tumor-to-muscle ratio from the calculated radioactivity level in the tumor, radioactivity level in the blood, and radioactivity level in the muscle.

Figure 6:
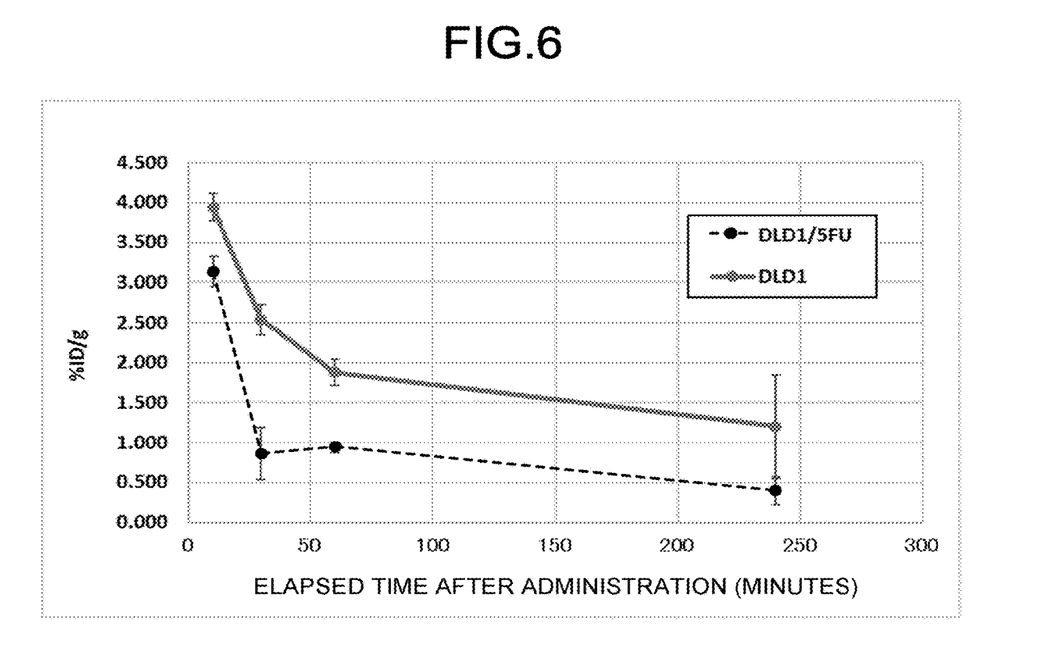
FIG. 6 is a graph illustrating a chronological change in the accumulation amount of [18F] in the tumor of DLD-1 mice and DLD-1/5-FU mice to which [18F]5-FU is administered.

As a result of comparison, in the DLD-1 mice, the average value (% ID/g) of the accumulation amount of [18F] was 2.0 times higher (see the point corresponding to elapsed time of 60 minutes after administration in the line graph illustrated in FIG. 6) than that in the DLD-1/5-FU mice. Moreover, the average value of the tumor-to-blood ratio in the DLD-1 mice was 1.6 times higher (see the bar graph corresponding to the inscription of "60 min" illustrated in FIG. 7) than that in the DLD-1/5-FU mice, and the average value of the tumor-to-muscle ratio in the DLD-1 mice was 1.9 times higher than that in the DLD-1/5-FU mice (see the bar graph corresponding to the inscription of "60 min" illustrated in FIG. 7). The values were all significantly high (p<0.01).

Figure 7:
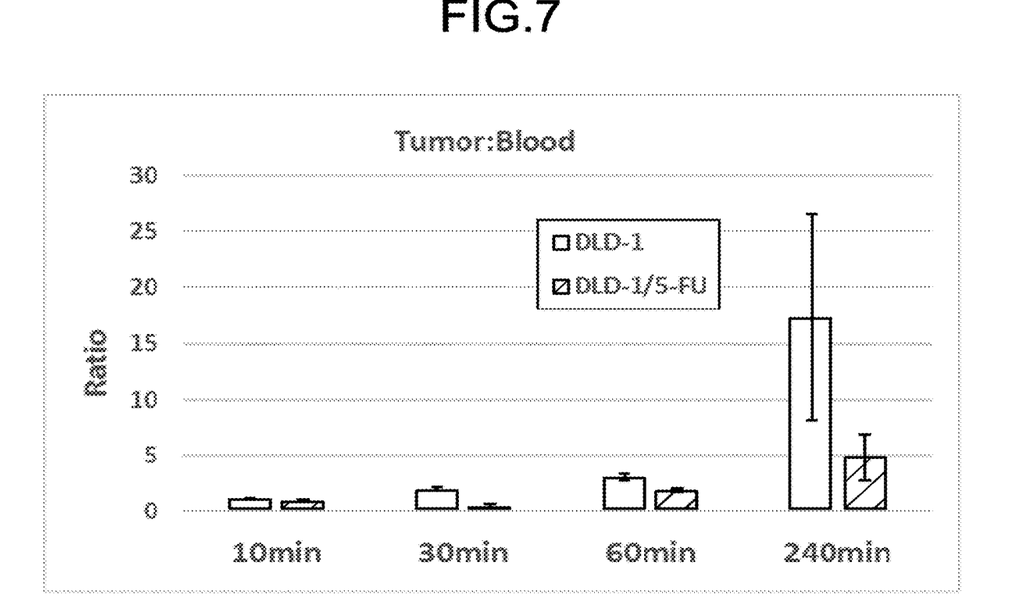
FIG. 7 is a graph illustrating a tumor-to-blood ratio in the DLD-1 mice and the DLD-1/5-FU mice, calculated from the radioactivity distribution in the tumor and blood.
Figure 8:
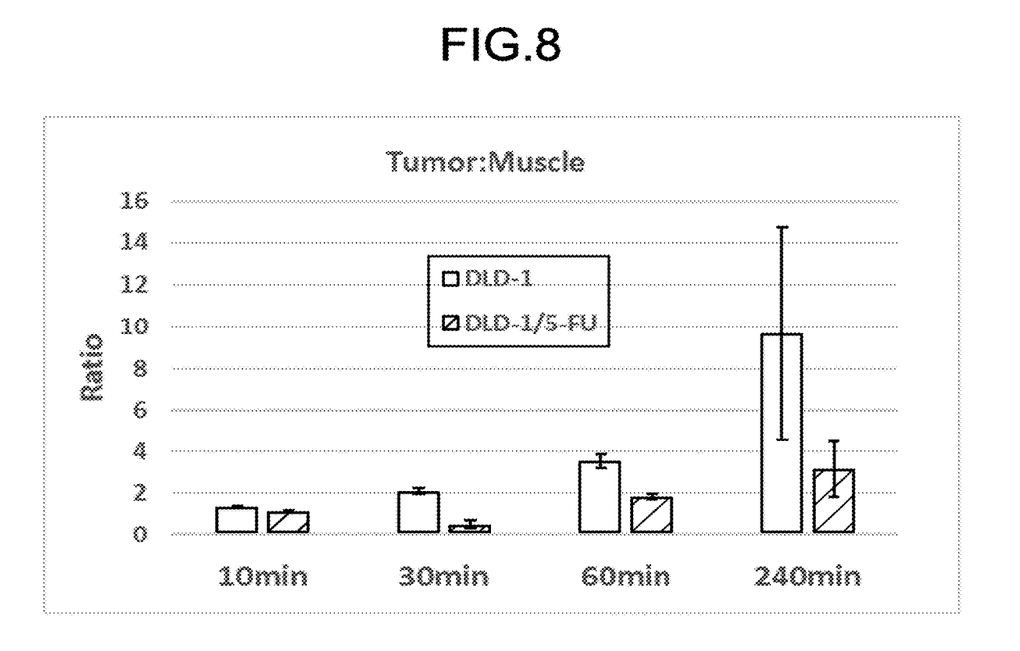
FIG. 8 is a graph illustrating a tumor-to-muscle ratio of the DLD-1 mice and the DLD-1 mice, calculated from the radioactivity distribution in the tumor and muscle.

As illustrated in FIG. 6, the accumulation amounts in the DLD-1 mice were also higher than those of the DLD-1/5-FU mice at 10 minutes after administration, 30 minutes after administration, and 240 minutes after administration. More specifically, the accumulation amounts in the DLD-1 mice were not significantly different from those in the DLD-1/5-FU mice, at 10 minutes after administration and at 240 minutes after administration. However, the accumulation amount in the DLD-1 mice was significantly higher than that in the DLD-1/5-FU mice at 30 minutes after administration (p<0.01). Moreover, as illustrated in FIG. 7 and FIG. 8, the tumor-to-blood ratio and the tumor-to-muscle ratio of the DLD-1 mice were also higher than those of the DLD-1/5-FU mice at 10 minutes after administration, 30 minutes after administration, and 240 minutes after administration. More specifically, the tumor-to-blood ratio and the tumor-to-muscle ratio of the DLD-1 mice were not significantly different from those of the DLD-1/5-FU mice at 10 minutes after administration and 240 minutes after administration. However, the tumor-to-blood ratio and the tumor-to-muscle ratio of the DLD-1 mice were significantly higher than those of the DLD-1/5-FU mice at 30 minutes after administration (p<0.01).

In Example 1 and Example 2, a correlation was found between the comparison results of the radioactivity distribution in the tissues in vivo obtained from the PET image, and the radioactivity distribution in the actual tissues in vivo. Consequently, it has become clear that it is possible to visualize the kinetics of 5-FU in vivo using [18F]5-FU, and evaluate the specificity of accumulation of [18F]5-FU in the tumor.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An analysis apparatus, comprising:
processing circuitry configured to
extract first, second, and third detection values in a tumor region, a blood region, and a muscle region, respectively, from a nuclear medicine image of a subject administered with a drug containing a radio-labeled anticancer drug that works by accumulating in a tumor;
calculate a first comparison value that is a comparison result between the second detection value in the blood region and the first detection value in the tumor region; and a second comparison value that is a comparison result between the third detection value in the muscle region and the first detection value in the tumor region; and
evaluate a specificity of accumulation of the drug in the tumor, based on the first comparison value and the second comparison value, wherein the specificity of accumulation of the drug in the tumor is evaluated based on (1) a first comparison result between the first comparison value and a threshold, and (2) a second comparison result between the second comparison value and the threshold.

2. The analysis apparatus according to claim 1, wherein the first comparison value is a ratio between the second detection value in the blood region and the first detection value in the tumor region.

3. The analysis apparatus according to claim 1, wherein the second comparison value is a ratio between the third detection value in the muscle region and the first detection value in the tumor region.

4. The analysis apparatus according to claim 1, wherein the processing circuitry is further configured to evaluate the specificity of the accumulation of [$^{18}$F]5-FU in the tumor.

5. The analysis apparatus according to claim 1, wherein the processing circuitry is further configured to (1) evaluate that the drug is easily accumulated in the tumor when the first comparison value and the second comparison value are both greater than the threshold, and (2) evaluate that the drug is not easily accumulated in the tumor when at least one of the first comparison value and the second comparison value is smaller than the threshold.

6. The analysis apparatus according to claim 1, wherein the processing circuitry is further configured to (1) evaluate that the drug is easily accumulated in the tumor when the first comparison value and the second comparison value are both greater than the threshold, (2) evaluate that the drug is moderately accumulated in the tumor when one of the first comparison value and the second comparison value is smaller than the threshold, and (3) evaluate that the drug is not easily accumulated in the tumor when both of the first comparison value and the second comparison value are smaller than the threshold.

7. A non-transitory computer-readable medium having stored thereon instructions that, when executed by a computer, cause the computer to perform:
   extracting first, second, and third detection values in a tumor region, a blood region, and a muscle region, respectively, from a nuclear medicine image of a subject administered with a drug containing a radiolabeled anticancer drug that works by accumulating in a tumor;
   calculating a first comparison value that is a comparison result between the second detection value in the blood region and the first detection value in the tumor region, and a second comparison value that is a comparison result between the third detection value in the muscle region and the first detection value in the tumor region; and
   evaluating a specificity of accumulation of the drug in the tumor, based on the first comparison value and the second comparison value, wherein the specificity of accumulation of the drug in the tumor is evaluated based on (1) a first comparison result between the first comparison value and a threshold, and (2) a second comparison result between the second comparison value and the threshold.

8. The non-transitory computer readable medium according to claim 7, wherein the instructions further cause the computer to evaluate the specificity of the accumulation of [$^{18}$F]5-FU in the tumor.

9. The non-transitory computer readable medium according to claim 7, wherein the instructions further cause the computer to (1) evaluate that the drug is easily accumulated in the tumor when the first comparison value and the second comparison value are both greater than the threshold, and (2) evaluate that the drug is not easily accumulated in the tumor when at least one of the first comparison value and the second comparison value is smaller than the threshold.

10. The non-transitory computer readable medium according to claim 7, wherein the instructions further cause the computer to (1) evaluate that the drug is easily accumulated in the tumor when the first comparison value and the second comparison value are both greater than the threshold, (2) evaluate that the drug is moderately accumulated in the tumor when one of the first comparison value and the second comparison value is smaller than the threshold, and (3) evaluate that the drug is not easily accumulated in the tumor when both of the first comparison value and the second comparison value are smaller than the threshold.

11. An analysis method executed by a computer, comprising:
   extracting first, second, and third detection values in a tumor region, a blood region, and a muscle region, respectively, from a nuclear medicine image of a subject administered with a drug containing a radiolabeled anticancer drug that works by accumulating in a tumor;
   calculating a first comparison value that is a comparison result between the second detection value in the blood region and the first detection value in the tumor region, and a second comparison value that is a comparison result between the third detection value in the muscle region and the first detection value in the tumor region; and
   evaluating a specificity of accumulation of the drug in the tumor, based on the first comparison value and the second comparison value, wherein the specificity of accumulation of the drug in the tumor is evaluated based on (1) a first comparison result between the first comparison value and a threshold, and (2) a second comparison result between the second comparison value and the threshold.

12. The analysis method according to claim 11, wherein the first comparison value is a ratio between the second detection value in the blood region and the first detection value in the tumor region.

13. The analysis method according to claim 11, wherein the second comparison value is a ratio between the third detection value in the muscle region and the first detection value in the tumor region.

14. The analysis method according to claim 11, wherein evaluating the specificity comprises evaluating the specificity of the accumulation of [$^{18}$F]5-FU in the tumor.

15. The analysis method according to claim 11, wherein evaluating the specificity comprises (1) evaluating that the drug is easily accumulated in the tumor when the first comparison value and the second comparison value are both greater than the threshold, and (2) evaluating that the drug is not easily accumulated in the tumor when at least one of the first comparison value and the second comparison value is smaller than the threshold.

16. The analysis method according to claim 11, wherein evaluating the specificity comprises (1) evaluating that the drug is easily accumulated in the tumor when the first comparison value and the second comparison value are both greater than the threshold, (2) evaluating that the drug is moderately accumulated in the tumor when one of the first comparison value and the second comparison value is smaller than the threshold, and (3) evaluating that the drug is not easily accumulated in the tumor when both of the first comparison value and the second comparison value are smaller than the threshold.

* * * * *